United States Patent [19]
Holland et al.

[11] Patent Number: 5,129,999
[45] Date of Patent: Jul. 14, 1992

[54] LENS DISINFECTOR AND METHOD

[75] Inventors: Gregory R. Holland, Irvine; Barrett E. Cloud, Orange, both of Calif.

[73] Assignee: Allergan, Inc., Irvine, Calif.

[21] Appl. No.: 592,668

[22] Filed: Oct. 4, 1990

[51] Int. Cl.⁵ ............................................. C25F 5/00
[52] U.S. Cl. ..................... 204/131; 204/130; 204/194; 204/242; 204/272; 204/276; 204/278; 204/DIG. 6; 206/51
[58] Field of Search ............... 204/130, 131, 149, 242, 204/193, 194, DIG. 6, 290 R, 291, 292, 272, 291, 292, 293, 276, 278; 206/5.1

[56] References Cited
U.S. PATENT DOCUMENTS

| Re. 32,672 | 5/1988 | Huth et al. ............................ 252/95 |
| 3,278,447 | 10/1966 | McNicholas ....................... 252/187 |
| 3,394,717 | 7/1968 | Hollinger .............................. 206/5.1 |
| 3,444,868 | 5/1969 | Hungerford et al. ................ 206/5.1 |
| 3,622,479 | 11/1971 | Schneider ........................... 204/149 |
| 3,910,296 | 10/1975 | Karageozian et al. ................. 134/2 |
| 3,912,451 | 10/1975 | Gaglia, Jr. .............................. 21/58 |
| 4,084,747 | 3/1978 | Alliger ................................... 239/4 |
| 4,104,190 | 8/1978 | Hartshorn ....................... 252/187 R |
| 4,202,740 | 5/1980 | Stoner et al. ........................ 204/130 |
| 4,236,992 | 12/1980 | Themy .................................. 204/278 |
| 4,361,471 | 11/1982 | Kosarek .............................. 204/120 |
| 4,499,077 | 2/1985 | Stockel et al. ...................... 424/149 |
| 4,557,925 | 12/1985 | Lindahl et al. ...................... 429/19 |
| 4,568,517 | 2/1986 | Kaspar et al. ........................ 422/30 |
| 4,614,549 | 7/1986 | Ogunbiyi et al. ..................... 134/19 |
| 4,654,208 | 3/1987 | Stockel et al. ....................... 424/78 |
| 4,689,215 | 8/1987 | Ratcliff ................................. 424/53 |
| 4,767,559 | 8/1988 | Kruse et al. ........................ 252/106 |

FOREIGN PATENT DOCUMENTS

| 1156420 | 11/1983 | Canada . |
| 0082798 | 6/1983 | European Pat. Off. . |
| 0147100 | 7/1985 | European Pat. Off. . |
| 0209071 | 1/1987 | European Pat. Off. . |
| 0255041 | 5/1988 | European Pat. Off. . |
| 0278224 | 8/1988 | European Pat. Off. . |
| 3626082 | 11/1988 | Fed. Rep. of Germany . |
| WO8504107 | 9/1985 | PCT Int'l Appl. . |
| WO8605695 | 10/1986 | PCT Int'l Appl. . |
| 2094992 | 9/1982 | United Kingdom . |
| 2151039 | 7/1984 | United Kingdom . |
| 2139260 | 11/1984 | United Kingdom . |
| 2173017 | 10/1986 | United Kingdom . |

OTHER PUBLICATIONS

Chemical Abstracts Selects: Issue 2, 1987; 106:9424f.
Eudragit L Data Sheet (Info L-2/e).
Stoner, et al., The Mechanism of Low Frequency a.c. Electrochemical Disinfection.

Primary Examiner—John Niebling
Assistant Examiner—Kathryn Gorgos
Attorney, Agent, or Firm—Frank J. Uxa, Jr.; Gordon L. Peterson

[57] ABSTRACT

An apparatus for disinfecting lenses includes a single hand-held case with a lens compartment and a power supply compartment. A battery powered unit disposed within the power supply compartment responds to activation of a switch on the case to generate an electric current which is coupled to a pair of electrodes within the lens compartment to electrolyte a solution in the lens compartment and thereby disinfect lenses submerged in the solution. Disinfecting proceeds using a buffered solution to retain solution pH within predefined limits while enabling electrolysis with a large current of shorter duration to decreased disinfecting time. A lip circumscribing an upper opening of the lens compartment is covered with a single hinged cover member that lifts directly away from the lip, and a slidable retainer member is used to retain the cover member in a closed position. Ribs on the cover member retain the lenses submerged in the solution, and a hydrophobic element discharges gases produced by electrolysis. An enlarged ruthenium coated anode enhances electrolytic action while inhibiting catalytic degradation, while timing circuitry and indicators on the case enhance operator convenience.

38 Claims, 3 Drawing Sheets

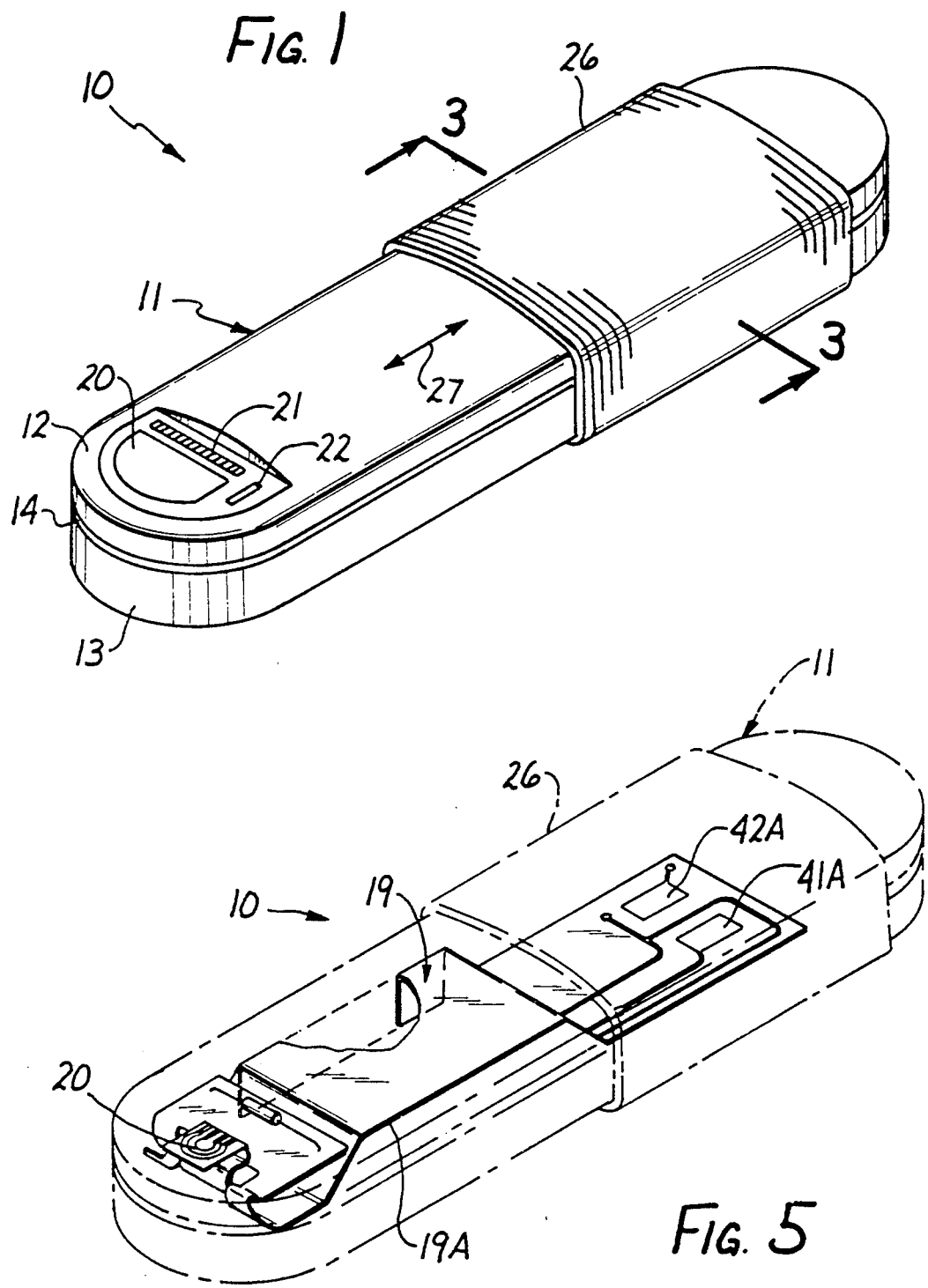

U.S. Patent    July 14, 1992    Sheet 2 of 3    5,129,999
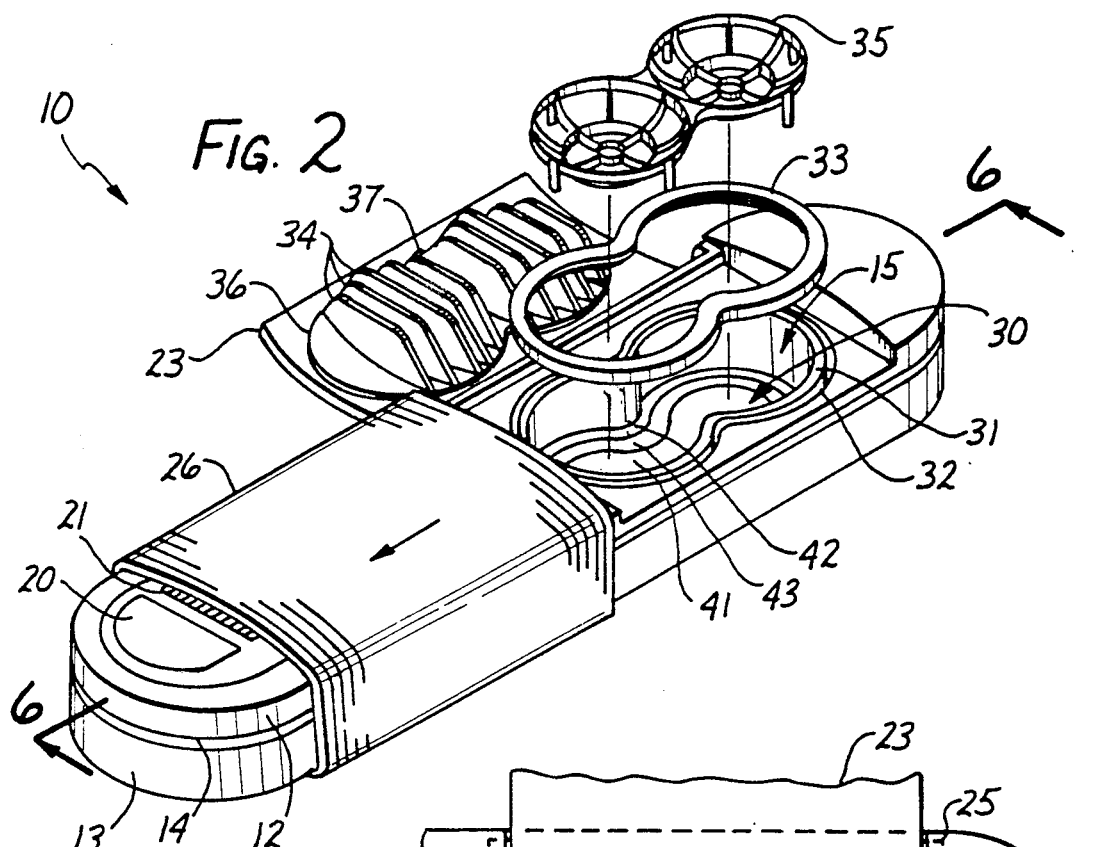
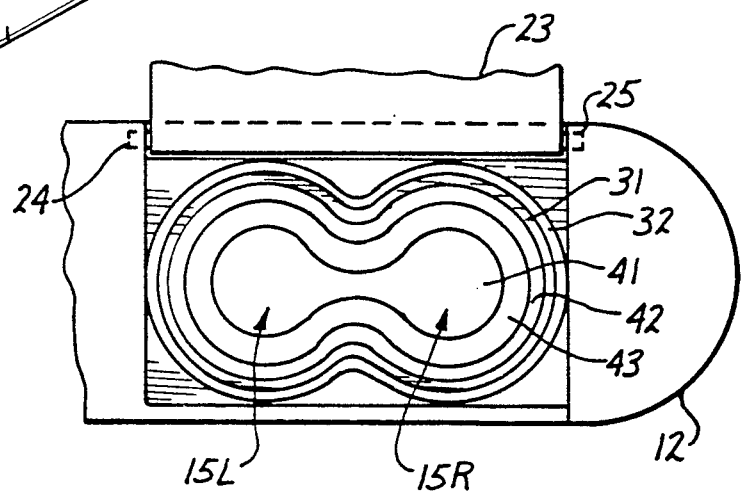
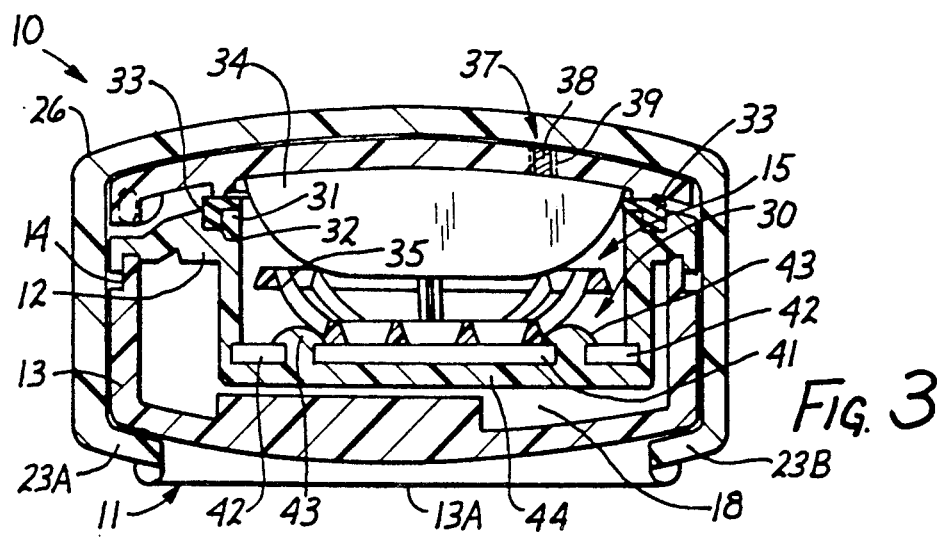

LENS DISINFECTOR AND METHOD

BACKGROUND OF THE INVENTION

1. Technical Field

This invention relates generally to lenses such as contact lenses, and more particularly to a new and improved apparatus and methodology for disinfecting such lenses.

2. Background Information

Contact lens disinfection involves deactivation or killing of microorganims on lenses and results in improved eye comfort and safety. Probably the oldest method of doing this is called heat disinfection, and it proceeds by heating the lenses while they are submerged in a suitable liquid within a lens case. In comparison, chemical disinfection involves bathing the lenses in low dosages of chemicals that are toxic to the microorganisms but not to the eye, and a typical oxidative disinfectant system utilizes a peroxide, such as hydrogen peroxide, to attack the unwanted microorganisms. In each case, disinfection is usually left to the contact lens owner to perform, most often at home between periods of lens usage and frequently as often as once or twice each day.

Depending on which technique is used, disinfection may take from approximately twenty minutes to four hours to accomplish. In addition, it often requires attention to various procedural details of little interest to many contact lens owners. Furthermore, the required lens cases, chemicals, and other disinfection paraphernalia often seem to complicate the process all the more, and lens owners often, simply forgo a recommended lens disinfecting regimen to avoid the inconvenience. Consequently, it is desirable to have a new and improved lens disinfecting apparatus that overcomes these concerns--one enabling quick and convenient disinfecting with little skill and effort.

One method cf reducing disinfecting time is described in U.S. Pat. No. 4,202,740 to Stoner. The Stoner patent describes an apparatus and method for disinfecting objects with an electrolytic process that takes three to five minutes. The lenses are held between a pair of electrically conductive members, and these members are then submerged in an electrolyte solution within an electrolytic cell. Then, a six to ten volt alternating current is impressed across a pair of electrodes in the cell, and this causes electrolytic disinfection of the lenses.

Thus, the Stoner patent discloses an electrolytic technique that decreases disinfecting time significantly. However, the particular design employed needs improvement. The time involved is still more than desirable for quick, on-the-spot disinfecting, and the structure employed is rather complex and unwieldy for use by the average contact lens owner.

Canadian Patent No. 1 156 420 to Tomei Sangyo Kabushikik Kaisha (inventors Tanaka, et al.) describes another method and apparatus for electrolytic disinfecting. The apparatus described in the Tomei patent includes a lens case that is similar in many respects to a conventional lens carrying case. However, the lens case includes a pair of electrodes at the bottom of each of two separate lens wells, and it is shaped and dimensioned to fit into an opening in a separate power supply unit.

When the carrying case is inserted into the opening, the electrodes become electrically connected to control circuitry within the power supply unit. By activating a power switch to turn on the power supply and a starter switch to begin the disinfecting cycle, a thirty second current pulse is passed through the electrodes, and this electrolyzes a physiologic saline solution in the lens wells to generate hypochlorite ions that disinfect the lenses. If desired, the cycle is repeated. Then, the carrying case is removed from the power supply unit, and the lenses removed from the carrying case for use.

The apparatus described in the Tomei patent presents certain concerns. For one, the power at the electrodes imposes a significant waiting period on the lens owner, and it would be advantageous to provide an apparatus that even further reduces the time required. In addition, the apparatus employs two units, both a lens case and a power supply, and sometimes one of the units becomes lost or is left behind. Also, the step of inserting the lens case into the power supply unit increases disinfecting time even more and involves more attention and manual dexterity than many lens owners would prefer. Thus, it would be advantageous to have an apparatus that overcomes these concerns as well.

The system of the Tomei patent has two wells, and each one must be opened to replenish the solution within or gain access to the lenses. Besides the time involved, the type of cover employed over each of the lens wells tends to wipe across the lip of the well when removed, and this often transfers contaminants to the interior. Although some existing lens cases have hinged covers with snap-on locking arrangements, these may be relatively difficult to operate so that a wiping action results between the cover and lip that transfers contaminants also. Furthermore, the relatively small electrodes within the lens wells limit electrolysis by virtue of their small surface area, and they tend to concentrate electrolysis at a central bottom region of the well around the anode. This is somewhat inefficient. Also, the bubbles produced as the solution is electrolyzed tend to lift the lenses to the upper surface of the solution where the disinfecting action is less effective.

Consequently, it would be advantageous to have a new apparatus for disinfecting lenses that overcomes these and other concerns to be described--one that is conveniently carried and operated to provide quick, portable, and reliable on-the-spot lens disinfecting.

SUMMARY OF THE INVENTION

This invention recognizes the problems associated with the prior art and provides a new lens disinfecting apparatus with the desired attributes.

Briefly, the above and further objects of the present invention are realized by providing an apparatus that combines both an electrolytic disinfecting unit and a lens compartment in a single portable case with numerous desirable features. In addition, the new method of disinfecting lenses according to the invention employs a shorter current pulse of increased magnitude to significantly reduce disinfecting time, and a buffered saline solution to maintain solution pH within predefined limits.

Generally, the apparatus includes a case having a size and shape adapted to be hand held. A first portion of the case defines an upwardly opening first compartment having a size and shape adapted to containing a quantity of solution and a pair of lenses within the solution. A pair of electrodes are disposed at a bottom portion of the first compartment, and a second portion of the case defines a second compartment in which is disposed a power supply unit for supplying an electric current to the electrodes to electrolyze at least a portion of the quantity of solution. A switch mounted on the case is used to activate the power supply unit selectively to thereby selectively disinfect the lenses.

Disinfecting preferably proceeds using a buffered solution to enable a controlled current pulse to generate a known concentration of active disinfectant or disinfectants while retaining solution pH within predefined limits. Thus, the disinfecting cycle can be reduced to even less than ten seconds. In one form of the invention, the disinfecting cycle is set at about ten seconds to about fifteen seconds to provide time for an operator to recognize that disinfecting has occurred.

According to one aspect of the invention, the first portion of the case includes a rim circumscribing the upper opening of the first compartment to enable closure of the first compartment with a single cover member. Thus, the lens owner need operate only one cover member. In addition, a suitably sized cover member is mounted on the case with a hinge so that it can be moved between an open position enabling access to the first compartment and a closed position covering the upper opening in generally fluid tight engagement of the lip. Thus, the cover member lifts directly away from the rim to inhibit transfer of contaminants as the lens case is opened.

The cover member preferably includes a plurality of spaced-apart ribs adapted to extend downwardly into the compartment when the cover member is in the closed position. The ribs act to assist retaining the lenses submerged in the solution. Also, a hydrophobic filter element disposed within a vent hole in the cover member discharges gas produced from the more vigorous electrolytic action while inhibiting the passage of the solution.

Another aspect of the invention includes a retaining member for selectively retaining the cover in the closed position. The retainer member has a size and shape adapted to span the cover member, and it is mounted on the case so that with the cover member in the closed position the retainer member can be slid between a first position enabling the cover member to be moved to the open position and a second position in which the retainer member is disposed over the cover member to secure it in the closed position. The cover member may be in the form of a sleeve having a size and shape adapted to conform to the contour of the exterior of an elongated case so that it can be slid over the case exterior between the first and second positions. Thus, a conveniently operated cover and cover locking arrangement is achieved.

Yet another aspect of the invention provides an enlarged first electrode that facilitates rapid electrolysis. The first electrode is in the form of an electrically conductive plate disposed over a substantial area at the bottom portion of the first compartment to serve as an anode, and it may be composed of a titanium material coated with a platinum group metal compound, in particular a ruthenium compound, which may enhance, through catalytic action, the degradation of the chemical species formed. The second electrode, e.g., titanium or stainless steel, is in the form of an electrically conductive ring circumscribing the first electrode that serves as the cathode.

Other materials, e.g., metals, metal oxides and the like, may be employed in the first electrode 41 and/or second electrode 42 provided that such other material or materials are electrically compatible, are effective in the present system, are substantially resistant to the environment or environments to which such electrodes are exposed, and have no substantial detrimental effect on the disinfection process or on the objects, e.g., contact lenses, being disinfected. Such other materials include, for example carbon, nickel, silver, gold and the like.

With this configuration, electrolysis occurs over a larger area and thus more quickly. Also, the disinfectant produced is dispersed more uniformly throughout the solution for more effective disinfecting. This results from the production of active disinfecting species over a larger surface area, and from the associated production of gas. The resulting upward flow of gas bubbles stirs the solution, so that a far more efficient disinfecting cycle is achieved. Moreover, disinfecting both lenses in the first compartment, instead of using separate lens wells, eliminates structural components and the need for duplicating the electrolytic process in each well.

The power supply unit includes a switch, a battery connector, and a complement of current generating components responsive to activation of the switch. When the switch is activated, the current generating components generate an electric current of a predetermined duration from electrical power supplied by a battery connected to the battery connector. The current is coupled to the electrodes and passed through the solution to produce one or more disinfectants which disinfect the lenses, and this is accomplished with the activation of only the one switch. Indicators further enhance operator convenience by providing a first human sensible signal during the disinfecting cycle and a second human sensible signal indicative of a low battery condition.

Thus, the apparatus of this invention overcomes many drawbacks of existing devices. It integrates the various components in a conveniently operated lens carrying case with numerous innovations, and provides a method of electrolytically disinfecting lenses, preferably in a buffered solution, that takes far less time.

Unlike existing devices, there is only one unit so that the tendency for a second unit to become lost or left behind is overcome. The step of inserting the lens case into the power supply unit is eliminated, thereby decreasing the time and increasing convenience. The case itself is much easier to use, having only one well and one cover to manipulate.

Furthermore, the cover is preferably hinged so that there is less likelihood of transferring contaminants. The slidable retainer member operates easily and smoothly without causing the solution to splash out of the lens compartment. The enlarged electrodes improve electrolytic action and dispersion within the lens compartment, and the ribs on the cover retain the lenses advantageously submerged.

With these features, the timing and indicator arrangements, and other innovations to be described, this invention achieves an apparatus for electrolytically disinfecting lenses in significantly less time.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 1 of the drawings is a perspective view of an apparatus constructed according to the invention;

FIG. 2 is a partially exploded perspective view showing details of the lens compartment;

FIG. 3 is an enlarged cross sectional view taken on line 3—3 of FIG. 1;

FIG. 4 is an enlarged plan view of a portion of the apparatus with the cover open to show the electrodes at the bottom of the lens compartment;

FIG. 5 is a perspective view of the membrane circuit board as it is mounted within the apparatus case (depicted in phantom lines);

DETAILED DESCRIPTION OF THE DRAWINGS

Figure 6:
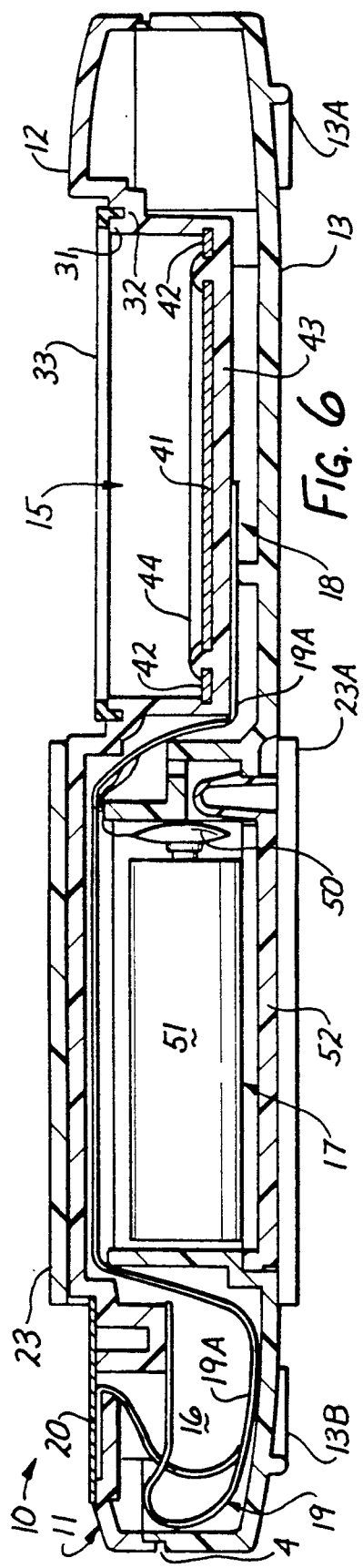
FIG. 6 is an enlarged cross sectional view of the apparatus taken on line 6—6 of FIG. 2.

Referring now to the drawings, there is shown a new apparatus 10 constructed according to the invention. Generally, the apparatus 10 comprises a body or case 11 including an upper member or first portion 12 and a lower member or second portion 13 attached together along seam 14. The first and second portions 12 and 13 are of suitable composition, such as polystyrene, fabricated according to known techniques, such as injection molding, and they are bonded together or otherwise suitably attached along the seam 14.

Together they form the elongated, hand-held case 11 having a size and shape adapted to be grasped in the hand as a convenient combination carrying case and lens disinfecting apparatus. The illustrated embodiment is approximately eighteen centimeters long, four centimeters wide, and two centimeters deep, although these dimensions are not critical.

The first portion 12 defines a first compartment or lens well 15 in which to contain a pair of contact lenses in saline solution (FIGS. 3-4 and 6), and the second portion 13 defines a second compartment or power unit compartment including a rearward portion 16, an intermediate portion 17, and a forward portion 18 (FIG. 6) in which to contain a power unit 19. The power unit 19 employs a membrane circuit board 19A disposed within the rearward, intermediate, and forward portions 16-18 according to known techniques (FIGS. 5 and 6) to generate an electrical current that is supplied to the lens well 15 for electrolytic disinfecting purposes.

Depressing the pushbutton switch 20 (FIG. 1) activates the power unit 19 for a few seconds and this results in disinfectant or disinfectants, e.g., chlorine and/or hypochlorous acid, being formed in the solution in the lens well 15 (not shown) and the lenses in the lens well being effectively disinfected. First indicator 21 signals that a disinfecting cycle is in progress, and second interior 22 signals a low battery condition. The disinfecting cycle may continue for a period of time after the current is stopped. For example, some additional time, e.g., on the order of about 10 seconds or less to about 20 minutes or more, may be useful after the electric current is stopped to allow for the disinfecting of the lens, e.g., contact lens, to be completed.

A hinged cover member or cover 23 (FIG. 2) is used to cover the lens well 15. It is mounted on the case 11 by suitable means such as protrusions extending from the cover 23 (not shown) that fit in mating recesses 24 and 25 on the case 11 (FIG. 4). The cover 23 can be moved between an open position, such as illustrated in FIG. 2, and a closed position covering the lens well 15. Thus, only one cover need be manipulated, and operation is relatively easy.

For further ease of operation, the apparatus 10 includes a slidable retainer member or sleeve 26 to retain the cover member 23 in the closed position. The sleeve 26 has a size and shape adapted to fit over the exterior of the case 11 so that it can be slid along the direction of the arrow 27 in FIG. 1 for this purpose. Of course other slidable arrangements can be utilized without departing from the inventive concepts embodied in the apparatus 10.

The sleeve 26 may be fabricated from a suitable thermoplastic composition injected molded to the desired configuration. The illustrated embodiment employs a resilient polyacetate composition that is dissimilar from the case 11, and this results in a low coefficient of friction between the case 11 and sleeve 26 so that the sleeve 26 operates all the more easily. The sleeve 26 is grasped with the fingers or hand and slid between a first position as illustrated in FIG. 2 that enables access to the lens well 15 and a second position as illustrated in FIG. 1 in which the cover member 23 is retained in the closed position.

Thus, the apparatus 10 provides an easily operated, conveniently transported disinfecting apparatus having only one lens well, one lens cover, and one unlocking apparatus combined in just one integrated case, and disinfection is accomplished by simply depressing a single switch. Although the illustrated embodiment accomplishes this with a specific design, the inventive concepts disclosed are equally applicable to any of various other sizes, shapes, and combinations that may be devised.

Considering the lens well 15 in further detail, it is in the form of an upwardly opening compartment or chamber having a left section 15L and a right section 15R (FIG. 4). Each one of the sections 15L and 15R is shaped and dimensioned to contain a quantity of solution and a lens immersed in the solution. As an idea of size, the sections 15L and 15R are each circularly-shaped with a diameter of approximately twenty seven millimeters and a depth of approximately twelve millimeters, and they combine to form the single, figure-eight-shaped lens well 15 illustrated. Thus, the lens well 15 can contain an optimum quantity of solution, and the solution can circulate freely between the two sections unimpeded for more effective disinfecting.

The lens well 15 extends from a lower portion 30 to a lip 31. The lip 31 circumscribes the lens well 15 to provide a surface facing the cover 23. The lip 31 is, in turn, circumscribed by a groove 32 that receives an elastomeric sealing member 33 composed of suitable material such as medical grade silicone rubber. The cover 23 is in the closed position, and so disposed, the ribs 34 serve the function of retaining lenses (not shown) immersed in a solution placed in the lens well 15, within a lens basket 35.

The lenses are retained loosely so that they do not float on bubbles produced during electrolysis. They are not held tightly against the basket 35, however. In this manner, the basket 35 and arrangement of the ribs 34 provides advantages over the trapping basket technique used in some prior art devices. The basket 15 is fabricated of a suitable composition such as a medical grade polystyrene.

When the cover 23 is moved to the closed position, a downwardly-extending ridge 36 on the cover 23 in a position circumscribing the ribs 34 contacts the sealing member 33 in high-pressure-per-unit sealing engagement. This keeps solution from leaking out of the lens well 15 when the cover 23 is closed. A vent 37 in the cover 23 including a filter element 38 disposed within a hole 39 in the cover 23 (FIG. 4) serves the function of discharging gas from the lens well while blocking passage of the solution. The element 38 may be a 0.22 micron hydrophobic filter of the type manufactured by Gelman Sciences of Ann Arbor Michigan. This element passes gas, but not liquid under less pressure than thirty pounds per square inch.

A pair of electrodes are disposed within the lens well 15. They include a first electrode or relatively broad, electrically conductive plate 41 and a second electrode or electrically conductive ring 42 circumscribing the first electrode 41. The first electrode 41 serves as an anode, and it is provided in the form of a relatively broad plate to increase the anode surface area at which electrolysis takes place. The second electrode 42 serves as the cathode, and the electrodes 41 and 42 are separated by an electrically nonconductive isolating ring 43 that is part of the bottom 44 in which the electrodes 41 and 42 are imbedded.

The figure eight shape of the first electrode 41 is approximately fifteen millimeters in diameter at each of its loops. This provides increased surface area while protecting against current flow between the electrodes 41 and 42 over the isolating ring 43. This helps increase the rate at which electrolysis can proceed. Each one of the electrodes 41 and 42 is connected electrically to the power unit 19 by suitable means, such as a pair of electrically conductive terminals 41A and 42A (FIG. 5) on the membrane circuit board 19A.

The circuit board 19A and the terminals 41A and 42A are not visible in FIG. 3, but the terminals 41A and 42A are connected electrically to respective one of the electrodes 41 and 42 by suitable means through holes in the bottom 44 (not shown).

The power unit 19 includes a battery connector 50 with which to connect a nine-volt battery 51 to the power unit 19 as a source of electrical power. The battery 51 is placed in the intermediate compartment 19, and a hinged battery compartment lid 52 is closed to secure the battery 51 in place.

Figure 7:
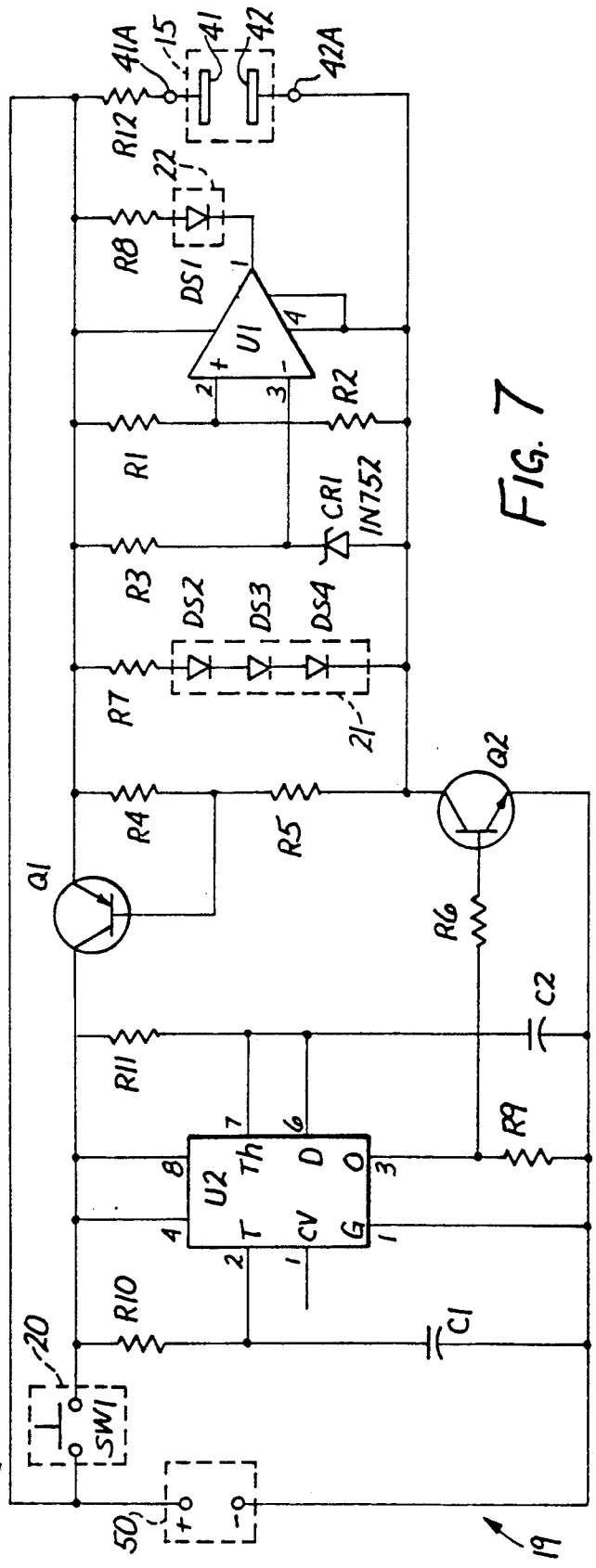
FIG. 7 is a schematic circuit diagram of the power supply unit employed in the apparatus.

The circuitry employed in the power unit 19 is shown in the schematic circuit diagram of FIG. 7. The membrane circuit board 19A is laced through the second compartment portions 16-18 as illustrated in FIG. 6 so that the switch 20, indicators 21 and 22, and electrodes 41 and 42 are electrically connected to the membrane board 19A. These components and the battery connector 50 are enclosed in dashed lines in FIG. 7 to highlight their position.

When the membrane switch 20 is depressed, power is supplied from the nine-volt battery 51. The membrane switch 20 is of the momentary-contact type, and depressing it causes current to be supplied to a timer integrated circuit U2 wired as a monostable multivibrator. The period of U2 is dependent upon the values of a resistor R11 and a capacitor C2. These are selected to provide for the formation of a sufficient or disinfecting amount of disinfectant or disinfectants, they being in the illustrated apparatus 10 one megohm and 10 microfarads with a type 555 timer integrated circuit.

When the timer U2 is triggered by depressing switch 20 to close SW1, the base of the NPN transistor Q2 is biased high by the output of timer U2. This causes transistor Q2 to turn 'on'. Through this action, the base of the PNP transistor Q1 is biased low, and switches 'on' to supply power to the timer after SW1 is opened.

Also, the transistor Q2 functions as a switch to perform several functions. First, it provides for a current return path to the battery 51 enabling the operation of other circuit components. Second, it illuminates the disinfection cycle LED indicators DS2, DS3 and DS4 (first indicator 21). Third, it permits current to flow through the lens well 15 and thus produce active disinfecting species from the saline in the cell. Fourth, it activates a type 311 comparator integrated circuit U1 wired as a voltage comparator, with a 1N752 zener diode CR1 providing a reference voltage of approximately 5.6 volts to the inverting input of the voltage comparator U1.

The positive voltage from the battery 51 is connected via the positive terminal on connector 50 to the noninverting input of the voltage comparator U1 through a resistor voltage divider consisting of resistors R1 and R2. The comparator U1 is triggered by a battery voltage of less than about 7.5 volts. When this occurs, the output on pin 7 of the comparator U1 goes to ground potential and illuminates the low battery LED indicator DS1 (second indicator 22).

A current-limiting resistor R12 in series with the contact 41A leading to the anode or first electrode 41, serves to limit the current to the cell. Resistors R8 and R7 are current-limiting resistors in series with the LED indicators.

Thus, the power unit 19 combines several conventional components to generate the desired current in response to the momentary depression of a single switch. It limits the current to a desired range, and provides convenient indicators of the disinfecting cycle and a low battery condition. Although the techniques employed may be known in a general sense for certain other applications, they have never been combined in this manner in an electrolytic lens disinfector. Combined in this manner, a very user-friendly apparatus results.

Generally, the electrochemistry system of the invention utilizes a low voltage, such as in the range of about 2.1 to about 6.5 volts DC, at relatively high currents, such as in the range of about 50 to about 150 milliamperes, across the first and second electrodes 41 and 42 in a buffered saline solution to produce hypochlorous acid (HOCl) and chloride radical (Cl$^-$). The system is capable of effective lens disinfection in significantly reduced times, e.g., relative to certain prior art devices.

However, the disinfecting cycle has been prolonged in the illustrated embodiment to twelve and one-half seconds so that the user will think something has happened and not depress the pushbutton switch 20 twice in succession. The disinfecting cycle can be even further prolonged within certain aspects of the invention to about one minute or more. This is done by reducing the current level during the disinfecting cycle, and among other things, reduces the amount of buffering required to maintain an eye-tolerable solution pH. Additional time, after the current is stopped (after the disinfecting cycle), may be useful so that the electrolytically produced disinfectant or disinfectants can effectively disinfect the lenses.

Anode or first electrode 41 composition is particularly significant. It is a titanium with a black surface coating of ruthenium dioxide one micron thick. The cathode or second electrode 42 can be any corrosion resistent electrode material such as titanium or stainless steel. This overcomes the tendency of other known electrode materials to either break down with time (catalytic degradation) or be prohibitively expensive (such as platinum).

The composition of the first electrode 41 aids in the catalysis of the degradation of the active species formed. Overnight essentially all of the reacted saline converts back to the original saline solution.

Use of the low voltage and relatively high currents runs counter to most existing chlorine type generators, and it enables the apparatus 10 to work faster and be battery powered.

Several types of chemical disinfecting solutions may be used, involving halogens such as chlorine or bromine of one form or the other, that could be used for disinfection. The most desirable of these are those which activate for a short period to time, however long enough to effect adequate disinfection, and then quickly degrade to form some innocuous solution which would be physiologically compatible with the eye.

One such solution, a buffered saline solution, maintains proper pH control. It includes a buffer, e.g., .02 molar phosphate buffer, designed to maintain solution pH at about 7.4. The normal pH of the eye is about 7.2, the pH attained by unbuffered electrolysis at current levels of about 100 to about 150 milliamperes may reach about 11 or so, but with the buffer of this invention the pH is maintained within acceptable limits, in particular less than 7.5. A specific example of such a buffered saline solution is a non-preserved saline solution contain 0.8% by weight NaCl with the phosphate buffer.

The saline solution in the lens well is electrolyzed at a set current generated by the power unit 19 for a brief period of time, producing enough active species to cause effective lens disinfection. Electrolysis of chloride ion to chlorine proceeds by the following process:

1) Anodic reaction:

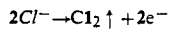
$2Cl^- \rightarrow Cl_2 \uparrow + 2e^-$

2) Cathodic reduction:

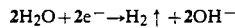
$2H_2O + 2e^- \rightarrow H_2 \uparrow + 2OH^-$

3) Net Reaction:

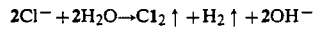
$2Cl^- + 2H_2O \rightarrow Cl_2 \uparrow + H_2 \uparrow + 2OH^-$

The formation of $Cl_2$ by electrolysis from a saline solution (0.9% sodium chloride) using an apparatus similar to the illustrated embodiment has been confirmed. The oxidation of chloride to $Cl_2$ occurs at the anode, and this produces bubbles of gas with the characteristic odor of $Cl_2$. Hydrogen gas forms at the cathode. The hydroxide ion ($OH^-$), the other reaction product at the cathode causes the pH to rise. A change of pH of the saline solution from a pH of 7.0 before electrolysis to a pH of 9 to 11 after electrolysis is common.

Chlorine can undergo further reaction to form primarily hypochlorite ion ($OCl^-$) in basic solution at a pH greater than 8. The disproportionation of $OCl^-$ to form chlorate ($ClO_3^-$) is slow at room temperature. Chlorate generally does not form perchlorate ($ClO_4^-$) at room temperature (23° C.) since this reaction takes place only very slowly, even near 100° C. The further reactions are as follows:

4) Further reaction:

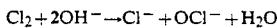
$Cl_2 + 2OH^- \rightarrow Cl^- + OCl^- + H_2O$ and primarily hypochlorous acid (HOCl) in neutral or acidic solution:

5) Further reaction:

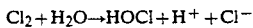
$Cl_2 + H_2O \rightarrow HOCl + H^+ + Cl^-$

6) Net Reaction (equilibrium):

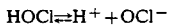
$HOCl \rightleftharpoons H^+ + OCl^-$

The saline solution is buffered at a pH of about 7.5. At this pH, the distribution of HOCl and $OCl^-$ in solution is about equal (50%/50%). Higher oxidation states of chlorine have not been observed in this process.

Using cyclic voltammetry and liquid chromatography with an electrochemical detector, $OCl^-$ ion has been identified after electrolysis. The presence of $ClO_3^-$ has been tested for, but it has not been detected in the electrolyzed solution.

Chlorous acid (HOClO) and chlorite ($OClO^-$) salts should not form in the electrolytic cell. These are formed from chlorine dioxide ($ClO_2$) which is not present.

The active chlorine produced diffuses through the saline solution, and degrades spontaneously upon standing. The chlorine degrades to substantially zero in about 6 to 12 hours.

Thus, the apparatus 10 can use available chlorine to disinfect soft contact lens. Available chlorine is produced by the electrolysis of sodium chloride solution. Upon standing in the electrolytic cell, available chlorine in the electrolyzed solution decays slowly. The following Table A below shows degradation of available chlorine versus time.

| DECAY OF TOTAL AVAILABLE CHLORINE | | | |
|---|---|---|---|
| Time (Min.) | Trial 1 (mg/L) | Trial 2 (mg/L) | Trial 3 (mg/L) |
| 0 | 21.9 | 23.7 | 17.8 |
| 10 | 19.9 | 19.6 | 13.9 |
| 60 | 14.2 | 12.4 | 10.1 |
| 180 | 4.7 | 6.5 | 8.4 |
| 360 | 1.2 | 2.8 | 4.0 |
| 720 | none detected | none detected | none detected |

Another type of solution which could be used involves the use of solutions of stabilized chlorine dioxide or chlorite solutions. The chlorite solutions can produce, under electrolysis, chlorine dioxide, a very effective antimicrobial agent. An advantage of chlorine dioxide is that it can effect a large kill of organisms at concentrations in solution of less than one part per million. As in the previously described sodium chloride solution, the buffering of the solution can control the type of active oxidative species which are produced, and the degradation species.

Description of the chemistry is as follows.

The oxidative half-reaction at the anode that occurs:

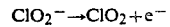
$ClO_2^- \rightarrow ClO_2 + e^-$

The reduction half-reaction at the cathode that occurs:

$2H_2O + 2e^- \rightarrow H_2 + 2OH^-$

Operationally, the contact lens to be disinfected may be first cleaned with a lens cleaner, e.g., an enzymatic lens cleaner.

In a particularly useful embodiment, the contact lens may be subjected to the action of at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from enzymes which are conventionally employed in the enzymatic cleaning of contact lenses. For example, many of the enzymes disclosed in Huth et. al. U.S. Patent RE 32,672 and Karageozian et al U.S. Pat. No. 3,910,296 are useful in the present invention. Each of these patents is incorporated in its entirety by reference herein. Among the useful enzymes are those selected from proteolytic enzymes, lipases, carbohydrate-active enzymes, e.g., carbolytic enzymes, and mixtures thereof.

Preferred proteclytic enzymes are those which are substantially free of sulfhydryl groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacteria and Asperigillus molds. Within this grouping, the still more preferred enzymes are the derived alkaline proteases generically called subtilisin enzymes. Reference is made to Deayl, L., Moser, P.W. and Wildi. B.S., "Proteases of the Genus Bacillus. II Alkaline Proteases", Biotechnology and Bioengineering, Vol. XII, pp 213-249 (1970) and Keay, L. and Moser, P.W., "Differentiation of Alkaline Proteases form Bacillus Species" Biochemical and Biophysical Research Comm., Vol 34, No. 5, pp 600-604, (1969).

The subtilisin enzymes are broken down onto two subclasses, subtilisin A and subtilisin B. In the subtilisin A grouping there are enzymes derived from such species are *B. subtilis, B. licheniformis* and *B. pumilis*. Organisms in this sub-class produce little or no neutral protease or amylase. The subtilisin B sub-class is made up of enzymes from such organisms a *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

If such an enzyme or enzymes are employed, an effective amount is preferably used. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

After cleaning, the lens or lenses are rinsed with saline solution to remove residual enzyme, and then placed into the lens well with about 8 milliliters of buffered saline solution. The cover is closed and the retainer slid along the case to secure the door.

The disinfection cycle is activated by pressing the single membrane switch on the exterior of the case, and the green LED indicator lights illuminate to indicate the disinfection cycle. At the end of the cycle, the lights go off. At this time, or after an additional period of time, e.g., about 10 seconds to about 20 minutes or more, has passed, the disinfected lenses can be removed. The lenses are then rinsed with a saline solution and can be worn.

Thus, this invention overcomes many drawbacks of existing devices. It integrates the various components in a conveniently operated lens carrying case with numerous innovations, and provides a method of electrolytically disinfecting lenses in a reduced period of time.

Unlike existing devices, there is only one unit so that the tendency for a second unit to become lost or left behind is overcome. The step of inserting the lens case into the power supply unit is eliminated, thereby decreasing time and increasing convenience. The case itself is much easier to use, having only one well and only one cover to manipulate.

Furthermore, the cover is hinged so that there is less likelihood of transferring contaminants. The slidable retainer member operates easily and smoothly without causing the solution to splash out of the lens compartment. The enlarged electrodes improve electrolytic action and dispersion within the lens compartment, and the ribs on the cover retain the lenses advantageously submerged.

Although an exemplary embodiment of the invention has been shown and described, many changes, modifications, and substitutions may be made by one having ordinary skill in the art without necessarily departing from the spirit and scope of the invention.

We claim:

1. An apparatus for disinfecting lenses, comprising:
   a case having a size and shape adapted to be held in the hand of a user and including permanently coupled first and second portions;
   the first portion of the case defining an upwardly opening first compartment having a size and shape adapted to contain a quantity of solution and a pair of lenses in side-by-side relationship with the solution;
   first and second electrodes disposed at a bottom portion of the first compartment;
   a power supply at least partially disposed within the second compartment and adapted to be activated to supply an electric current of the electrodes to electrolyze at least a portion of the quantity of solution; and a switch mounted on the case for use in activating the power supply.

2. An apparatus as recited in claim 1, wherein;

the first compartment extends from a closed bottom portion to an upper opening; and the first portion of the case includes a rim circumscribing the upper opening to enable closure of the first compartment with a single cover member.

3. An apparatus as recited in claim 2, further comprising:

a cover member having a size and shape adapted to cover the upper opening; and a hinge for mounting the cover member on the case so that the cover member can be moved between an open position enabling access to the first compartment and a closed position covering the upper opening in generally fluid tight engagement of the lip.

4. An apparatus as recited in claim 3, wherein the cover member includes:

a plurality of spaced-apart ribs adapted to extend downwardly into the first compartment when the cover member is in the closed position and acting to at least assist in retaining the lenses submerged in the solution.

5. An apparatus as recited in claim 3, wherein the cover member includes:

a vent, including a portion of the cover member defining a hole in which is disposed a hydrophobic filter element, for providing a vent enabling passage of gas generated in the first compartment during electrolytic disinfecting while inhibiting the passage of the solution.

6. An apparatus as recited in claim 3, further comprising:

a cover retainer to selectively retain the cover member in the closed position.

7. An apparatus as recited in claim 6, wherein the cover retainer includes:

a retainer member having a size and shape adapted to span the cover member; and a mounting assembly for mounting the cover retainer member on the case so that with the cover member in the closed position the retainer member is slidable between a first position enabling the cover member to be moved to the open position and a second position in which the retainer member is disposed over the cover member to thereby retain the cover member in the closed position.

8. An apparatus as recited in claim 7, wherein:

the case is an elongated member; and the retainer member is a sleeve having a size and shape adapted to conform to the contour of the exterior of the case and slide over the exterior of the case between the first and second positions.

9. An apparatus as recited in claim 8, wherein:

the retainer member is composed of a material dissimilar to the material of which the case is composed to thereby reduce the coefficient of friction between the retainer member and the case.

10. An apparatus as recited in claim 9, wherein:

the case is composed of a polystyrene material; and the retainer member is composed of a polyacetate material.

11. An apparatus as recited in claim 2, wherein:

the first compartment has a figure-eight-shaped cross sectional area in a transverse plane to define a separate section for each one of the lenses.

12. An apparatus as recited in claim 2, further comprising:

a basket, including a basket member having a size and shape adapted to fit within the first compartment, for supporting the lenses in side-by-side relationship within the first compartment slightly above the bottom portion of the first compartment, and for use in facilitating removal of the lenses from the first compartment.

13. An apparatus as recited in claim 1, wherein:

the first electrode is in the form of an electrically conductive plate disposed over a substantial central portion of the bottom portion of the first compartment to serve as an anode; and the second electrode is in the form of an electrically conductive ring circumscribing the first electrode to serve as a cathode.

14. An apparatus as recited in claim 13, wherein:

at least one of the electrodes is composed of a titanium material.

15. An apparatus as recited in claim 14, wherein:

the first electrode includes a coating composed of a ruthenium material.

16. An apparatus as recited in claim 1, wherein the power supply comprises:

a battery connector; and a current generator responsive to activation of the switch for generating an electric current of a predetermined duration from electrical power supplied from a separately supplied battery disposed in said second compartment and connected to the battery connector, and for coupling the electric current to the electrodes.

17. An apparatus as recited in claim 16, further comprising:

a first indicator for providing a human sensible signal during the duration of the current.

18. An apparatus as recited in claim 16, further comprising:

a second indicator for providing a human sensible signal indicative of a low battery condition.

19. An apparatus as recited in claim 16, wherein:

the current generator is adapted to generate a current within a range of about fifty to about one hundred fifty milliamperes.

20. An apparatus as recited in claim 16, wherein:

the current generator is adapted to generate a current for a period of time within a range of about ten seconds to about one minute.

21. An apparatus as recited in claim 16, wherein:

the current generator is adapted to generate a current for a period of time within a range of about ten to fifteen seconds.

22. An apparatus as recited in claim 16, further comprising:

a current limiter for limiting the flow of the electric current.

23. An apparatus as recited in claim 22, wherein:

the current limiter limits the flow of current to within a range of about fifty to about one hundred fifty milliamperes.

24. An apparatus as recited in claim 16, wherein:

the switch is in the form of a momentary-contact membrane switch.

25. An apparatus as recited in claim 16, wherein the current generator comprises:
a plurality of electrical components mounted on a membrane circuit board.

26. An apparatus for disinfecting contact lenses, comprising:
a case having a size and shape adapted to be held in the hand of a user and including permanently coupled first and second portions;
the first portion of the case defining an upwardly opening first compartment having a size and shape adapted to containing a quantity of solution and a pair of lenses within the solution;
first and second electrodes disposed at a bottom portion of the first compartment;
the second portion of the case defining a second compartment adapted to hold at least a portion of a power supply to supply an electric current to the electrodes to electrolyze at least a portion of the quantity of solution;
wherein the first compartment extends from a closed bottom portion to an upper opening and has a size and shape adapted to contain the pair of lenses in side-by-side relationship; and
the first portion of the case includes a rim circumscribing the upper opening to enable closure of the first compartment with a single cover member.

27. An apparatus as recited in claim 26 further comprising:
a cover member having a size and shape adapted to cover the upper opening; and
a hinge for mounting the cover member on the case so that the cover member is moveable between an open position enabling access to the first compartment and closed position covering the upper opening in generally fluid tight engagement of the lip.

28. An apparatus as recited in claim 27 wherein the cover member includes:
a plurality of spaced-apart ribs adapted to extend downwardly into the first compartment when the cover member is in the closed position and retain the lenses submerged in the solution.

29. An apparatus as recited in claim 27 wherein the cover member includes:
a vent, including a portion of the cover member defining a hole in which is disposed a hydrophobic filter element, for providing a vent enabling passage of gas generated in the first compartment during electrolytic disinfecting while inhibiting the passage of the solution.

30. An apparatus as recited in claim 26 wherein:
the first compartment has a figure-eight-shaped cross sectional area in a transverse plane to define a separate section for each one of the lenses.

31. An apparatus as recited in claim 26 further comprising:
a basket, including a basket member having a size and shape adapted to fit within the first compartment, for supporting the lenses in side-by-side relationship within the first compartment slightly above the bottom portion of the first compartment, and for use in facilitating removal of the lenses from the first compartment.

32. An apparatus as recited in claim 26 wherein:
the first electrode is in the form of an electrically conductive plate disposed over a substantial central portion of the bottom portion of the first compartment to serve as an anode; and
the second electrode is in the form of an electrically conductive ring circumscribing the first electrode to serve as a cathode.

33. An apparatus for disinfecting lenses, comprising:
a case having a size and shape adapted to be held in the hand of a user and including permanently coupled first and second portions;
the first portion of the case defining an upwardly opening first compartment having a size and shape adapted to containing a quantity of solution and a pair of lenses in side-by-side relationship within the solution;
first and second electrodes disposed at a bottom portion of the first compartment;
the second portion of the case defining a second compartment adapted to hold at least a portion of a power supply to supply an electric current to the electrodes to electrolyte at least a portion of the quantity of solution;
wherein the first electrode is in the form of an electrically conductive plate disposed over a substantial central portion of the bottom portion of the first compartment to serve as an anode; and
the second electrode is in the form of an electrically conductive ring circumscribing the first electrode to serve as a cathode.

34. A method of electrolytically disinfecting a pair of lenses, comprising:
placing the pair of lenses in side-by-side relationship in an upwardly opening first compartment in a case including a second compartment permanently coupled to the first compartment and adapted to hold at least a portion of a power supply; and
contacting the pair of lenses with a buffered physiological saline solution while passing an electric current supply by the power supply through the solution to form an effective amount of a disinfectant in the solution while maintaining solution pH within eye-tolerable levels.

35. A method as recited in claim 34
wherein the electric current is within the range of about 10 milliamperes to about 150 milliamperes and is passed through the solution for a period within the range of about 1 second to about 120 seconds.

36. A method as recited in claim 34 wherein the buffered saline solution has a pH of about 7.4.

37. A method as recited in claim 35 wherein the buffered saline solution includes about 0.8% by weight NaCl with a phosphate buffer.

38. A method as recited in claim 34 further comprising:
contacting the pair of lenses with at least one enzyme to remove debris from a contact lens in an amount effective to substantially remove at least one type of debris from the lens.

* * * * *

UNITED STATES PATENT AND TRADEMARK OFFICE
CERTIFICATE OF CORRECTION

PATENT NO. : 5,129,999
DATED : July 14, 1992
INVENTOR(S) : Gregory R. Holland et al It is certified that error appears in the above—identified patent and that said Letters Patent is hereby corrected as shown below:

In the Abstract at line 11, please change "large" to -- larger -- .

Column 8, line 42, delete "," between "they" and "have".

Column 12, line 63, change "with" to -- within -- .

Column 12, line 67, insert the following:

-- the second portion of the case defining a second compartment; --

Column 13, line 1, change "of" to -- to -- .

Signed and Sealed this

Fifth Day of October, 1993

Attest:

BRUCE LEHMAN

Attesting Officer     Commissioner of Patents and Trademarks